United States Patent [19]

Elgjo et al.

[11] Patent Number: 4,868,156
[45] Date of Patent: Sep. 19, 1989

[54] PHARMACEUTICAL PREPARATION CONTAINING A DIPEPTIDE WITH CELL GROWTH REGULATING EFFECT

[75] Inventors: Kjell Elgjo; Karl-Ludvig Reichelt, both of Oslo, Norway

[73] Assignee: Bio-Tech A/S, Oslo, Norway

[21] Appl. No.: 124,784

[22] PCT Filed: Feb. 26, 1987

[86] PCT No.: PCT/NO87/00015
§ 371 Date: Nov. 24, 1987
§ 102(e) Date: Nov. 24, 1987

[87] PCT Pub. No.: WO87/05219
PCT Pub. Date: Sep. 11, 1987

[30] Foreign Application Priority Data

Feb. 28, 1986 [NO] Norway .................................. 860751

[51] Int. Cl.⁴ .......................... A61K 37/02; C07K 7/04
[52] U.S. Cl. ....................................................... 514/19
[58] Field of Search .......................................... 514/19

[56] References Cited

U.S. PATENT DOCUMENTS 4,053,588 10/1977 Konig et al. ............................ 514/18
4,493,828 7/1985 Leung et al. ........................... 514/19

OTHER PUBLICATIONS

Yamada et al., Separation and Determination of Peptides by Liquid Chromatography, C.A. 1979, vol. 91, p. 104835w.

Primary Examiner—Lester L. Lee
Attorney, Agent, or Firm—Wenderoth, Lind & Ponack

[57] ABSTRACT

Method for treatment of abnormally fast rate of cell proliferation in the epidermis, by administration of a dipeptide of the formula

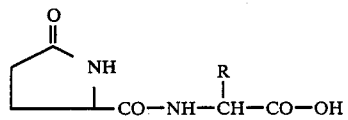

wherein R is H or CH₃, the pyroglutamic acid moiety being in the L-configuration, and the C-terminal amino acid moiety being in the D-configuration when R is methyl, and the C-terminal carboxyl group may be reduced to —CH$_2$—OH, or is in amide form —CO—NH$_2$, and cation complexes and physiologically acceptable acid addition salts thereof, the complexes being selected from complexes with Zn$^{++}$, Ca$^{++}$, Mg$^{++}$ and Mn$^{++}$.

2 Claims, No Drawings

PHARMACEUTICAL PREPARATION CONTAINING A DIPEPTIDE WITH CELL GROWTH REGULATING EFFECT

The present invention relates to a pharmaceutical composition containing a dipeptide which reversibly inhibits cell proliferation in squamous epithelia, and a process for preparing such a peptide.

Many skin disorders are characterized by an abnormally fast rate of cell proliferation in the epidermis. In this category of skin diseases, psoriasis is the one which has been best investigated. Here, cell proliferation takes place very rapidly, and the cells do not have sufficient time to mature normally and are shed from the surface while still containing their nucleus. In many other skin diseases the cell proliferation rate is markedly increased, but none of these have been subjected to such extensive studies as has psoriasis. High mitotic activity is also found in most benign and malignant skin tumors of epidermal origin.

Cell division (mitosis) in the normal epidermis is confined to the lowermost cell layer (the basal cell layer) facing the underlying layer of connective tissue (the dermis). After a basal cell has divided into two daughter cells, one of the daughter cells-on average-remains in the basal cell layer, while the other gradually matures (keratinizes) as it migrates through the various layers of the epidermis. It reaches the surface as a fully keratinized cell without a nucleus, and is eventually shed. In the adult epidermis the number of cells lost from the surface in a given time is exactly balanced by the production of new cells in the basal cell layer. It is only in this manner that a constant thickness of the epidermis can be maintained. If a large number of epidermal cells are suddenly lost, e.g. after injury, the rate of cell division in the basal cell layer increases after a short lag time. After a period of time which depends on the degree of cell loss, the epidermis regains its former, normal, thickness. Large series of experiments have indicated that the balance between cell loss and cell renewal in the epidermis is biologically regulated according to the negative feedback principle. In such a system, the maturing cells continuously produce an inhibitor which diffuses down to the basal cell layer where it inhibits the rate of cell proliferation. The concentration of inhibitor in the basal cell layer is dependent on the number of mature, or maturing cells. Thus, when mature cells are lost from the surface, the concentration of inhibitor decreases, allowing the basal cells to divide at a faster rate. This regulatory mechanism seems to be active to a certain extent even in malignant tumors.

We have now discovered that the keratinizing cells produce an inhibitor (or a group of inhibitors) which is of peptide nature. We have also been able to isolate and determine the structure of such compounds. In particular we have purified, identified and chemically synthesized a dipeptide which, when tested for biological activity in vivo, reversibly inhibits the rate of cell proliferation in the basal cell layer, e.g. upon administration to mice. Furthermore, in vitro experiments have demonstrated that cells of an established cell line are inhibited by this dipeptide at very low concentrations. This cell line originates from mouse epidermis treated with a skin carcinogen (DMBA). Continuous treatment in vitro will arrest cell proliferation completely for a period of several days in normal keratinizing epithelial cells, while transformed cells are only partially inhibited. In both cases the inhibition is completely reversible when the treatment is terminated. In vitro experiments have also demonstrated that both normal and transformed cells mature (keratinize) at a faster rate after a 24-hour treatment with one of the new pentapeptides. No toxic effects have been observed either in vivo or in vitro at the concentrations tested.

The dipeptides which have the above described effects, have the formula

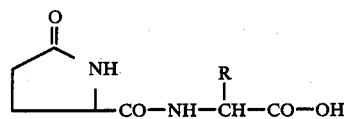

wherein R is H or CH₃, the pyroglutamic acid moiety (pGlu) being in the L-configuration, and the C-terminal amino acid moiety being in the D-configuration when R is methyl, and the C-terminal carboxyl group may be reduced to —CH$_2$—OH or is in amide from —CO—NH$_2$, and cation complexes and salts thereof.

Suitable cation complexes are particularly complexes with Zn$^{++}$, Ca$^{++}$, Mg$^{++}$ and Mn$^{++}$. Suitable salts are acid addition salts, such as hydrochlorides and alkali, alkaline earth and amine salts which are physiologically acceptable.

The dipeptides of formula I have been described as components in mushroom [J. Food Sci., Vol. 35 (1970), p. 134–9]. It is suggested that they may have something to do with the taste of mushroom, but apart from that no effect has been given.

The dipeptide pGlu-Gly is also described in Japanese Kokai 79 19968 (Application 77/82882) and 79 53597 (Application 77/119470) and in Arch. Biochem. Biiophys. 1985, 240(1), 178-83 (Shanghai) but without mention of any growth inhibiting effect. The dipeptide pGlu-D-Ala is described in Pept. Chem. 1978 (Pub. 1979) 16th, 131-4, but again without mention of growth inhibiting effect.

In the following Table 1 the in vivo result (change in mouse epidermal mitotic rate) has been described as an example for one of the dipeptides. The epidermal mitotic rate was measured for the first three hours after intraperitoneal injection of the dipeptide. Mitotic rate was determined by means of "Colcemid". A reduced rate was determined as a percentage in comparison with control animals from the same cage.

| Synthetic peptide | Decrease in mitotic rate % | Peptide concentration, Moles of peptide injected per mouse |
|---|---|---|
| pGlu-Gly | 40 | $10^{-13}$ |

The dipeptide may, in a per se known manner, be incorporated in pharmaceutical compositions, e.g. as tablets, injection solutions, nose-spray compositions or suppositories.

The compounds of formula I may be prepared by subjecting a compound of formula I wherein carboxyl groups or amino groups optionally present have been protected, to a treatment to remove the protective group(s).

During the synthesis of the dipeptide it is e.g. possible to use one of the classical coupling methods published in the comprehensive and well known peptide literature. In general any reactive group (e.g. amino, hydroxyl and/or carboxyl) which shall not participate in a peptide bond, should be kept protected during the entire synthesis, and the last step will accordingly be a deprotection of a completely protected derivative of the desired final product. For the coupling steps in which the individual protected amino acids are bound together, several different known methods may be used, and these have been described in detail in the comprehensive literature regarding peptide synthesis. However, it is preferable here to prepare the different peptides by means of the so called solid phase method, which is considered to be suitable for the preparation of oligopeptides and their analogues in a rapid manner and with good yields. In this method, which was first introduced by R. B. Merrifield in 1963, the growing peptide chain is kept attached to a solid polymer support, and the synthesis starts by binding the C-terminal amino acid to the polymer. The most common amino acids attached to a polymer support are today commercially available. The next amino acid is then coupled to this polymer-bound amino acid by a repeated cycle with deprotection, washing and coupling. In this manner the entire peptide is built up in a polymer-bound form, and in the last step the final product is split off from the polymer by means of a suitable reagent (usually hydrofluoric acid, HF). In the following a typical example of a solid phase peptide synthesis is described.

Polymer support:

As solid carrier the following may, for example be used- either
- chloromethylated polystyrene, cross-linked with 2% divinyl benzene, "mesh" size 200–400 with chloro substitution of 0.3–1.5 meq./g, or
- benzhydrylamine resin, also cross-linked with 2% divinyl benzene, "mesh" size 200–400 with NH$_2$ substitution of 0.3–1.5 meq./g.

In the following example a commercially available chloromethylated polymer to which amino group protected glycine has already been attached, is used.

EXAMPLE:

Synthesis of pGlu-Gly.

2 mmoles of Boc-Gly-Rx were used as starting material, and 0.90 g of pGlu were added according to the usual principles for solid peptide synthesis.

Abbreviations:
Boc=t-butoxy carbonyl
DCC=dicyclohexyl carbodiimide
Rx=polymer support
Gly=glycine
p-Glu=pyroglutamic acid Hydrogen fluoride treatment:

3.8 g of dried resin with dipeptide attached thereto were placed in a Kel-F reaction vessel and wetted with approximately 10 ml of anisole. The reaction vessel was cooled by means of dry-ice/acetone, and 40 ml of HF were distilled over into the reaction vessel. The polymer with dipeptide attached thereto was then stirred at 0° C. for 45 minutes, whereafter HF was removed by evaporation. The polymer was then washed with ether and extracted with 10% acetic acid, and the extract was lyophilized.

The dipeptide pGlu-D-Ala is prepared in a similar way. The dipeptides may be converted to their cation complexes or salts, and the carboxyl group may be reduced to CH$_2$—OH or amidated to CO—NH$_2$.

We claim:

1. A method for treatment of abnormally fast rate of cell proliferation in the epidermis of a subject, which comprises administering to the subject an effective amount of a dipeptide of the formula

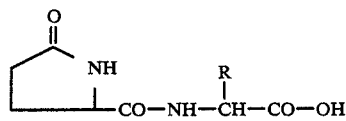

wherein R is H or CH$_3$, the pyroglutamic acid moiety being in the L-configuration, and the C-terminal amino acid moiety being in the D-configuration when R is methyl, and the C-terminal carboxyl group may be reduced to —CH$_2$—OH, or is in amide form —CO—NH$_2$, and cation complexes and physiologically acceptable acid addition salts thereof, the complexes being selected from complexes with Zn$^{++}$, Ca$^{++}$, Mg$^{++}$ and Mn$^{++}$.

2. The method of claim 1, wherein R is H.

* * * * *